US00PP24143P2

(12) United States Plant Patent
Collingwood

(10) Patent No.: US PP24,143 P2
(45) Date of Patent: Jan. 7, 2014

(54) ***CLEMATIS* PLANT NAMED 'SUZY MAC IMPROVED'**

(50) Latin Name: *Clematis patens*
Varietal Denomination: SUZY MAC IMPROVED

(76) Inventor: Brian Collingwood, Eccles (GB)

( * ) Notice: Subject to any disclaimer, the term of this patent is extended or adjusted under 35 U.S.C. 154(b) by 13 days.

(21) Appl. No.: 13/507,487

(22) Filed: Jul. 3, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Kent L Bell

(57) ABSTRACT

A new and distinct *Clematis patens* named 'SUZY MAC IMPROVED' is disclosed, characterized by a unusually abundant flowering, long flowering season. Plants are easy to grow in pots and in the ground, and easily propagated by vegetative cuttings. Plants are resistant to *Clematis* wilt. The new cultivar is a *Clematis* typically suited for ornamental container and landscape use.

1 Drawing Sheet

Latin name of the genus and species: *Clematis patens*.
Variety denomination: 'SUZY MAC IMPROVED'.

BACKGROUND OF THE INVENTION

The new cultivar is the result of a breeding program, resulting from a crossing made in May 1998. The inventor is Brian Collingwood, a citizen of the United Kingdom. The new variety was discovered as a seedling resulting from an open pollination of an unnamed, unpatented seed parent, *Clematis patens*, with an unidentified variety of *Clematis* as the pollen parent. The discovery was made in February 1999. Crossing and discovery was made at a private garden in Manchester, the United Kingdom.

After selecting and isolating the new cultivar, from approximately 60 seedlings resulting from the above mentioned open pollination, asexual reproduction of the new cultivar 'SUZY MAC IMPROVED' was first performed at a private garden in Manchester, the United Kingdom by vegetative cuttings in the January of 2001. The inventor maintained the original plant, and observed the asexually reproduced plants for several years, to establish stability of the characteristics. 'SUZY MAC IMPROVED' has since produced multiple generations and has shown that the unique features of this cultivar are stable and reproduced true to type.

SUMMARY OF THE INVENTION

The cultivar 'SUZY MAC IMPROVED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUZY MAC IMPROVED.' These characteristics in combination distinguish 'SUZY MAC IMPROVED' as a new and distinct *Clematis* cultivar:

1. Unusually abundant quantity of flowers.
2. Long flowering season.

3. Plants which are easy to grow both, in the ground, or in pots.
4. Ease of reproduction by vegetative cuttings.
5. Resistance to *Clematis* wilt.

PARENTAL COMPARISON

Plants of the new cultivar 'SUZY MAC IMPROVED' are similar to the seed parent variety in most horticultural characteristics. However, 'SUZY MAC IMPROVED' differs in having a more vigorous plant habit, larger flowers and more flowers per plant.

The pollen parent is unknown, a comparison cannot be made.

COMMERCIAL COMPARISON

Plants of the new cultivar 'SUZY MAC IMPROVED' are most similar to the commercial variety *Clematis* hybrid 'Burma star' unpatented. Both *Clematis* varieties have similar flower color and produce similar amounts of tepals. 'SUZY MAC IMPROVED' differs from 'Burma Star' in having a more vigorous plant habit, larger flowers and more flowers per plant. Addtionally, 'SUZY MAC IMPROVED' is easier to propagate than 'Burma Star'.

BRIEF DESCRIPTION OF THE PHOTOGRAPH

The accompanying photograph in FIG. 1 illustrates in full color a typical plant of 'SUZY MAC IMPROVED' grown outdoors in British Columbia, Canada. This plant is approximately 8 months old.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SUZY MAC IMPROVED' plants grown outdoors in Manchester, UK. Measurements were taken in Spring. The growing temperature ranged from approximately 2° C. to 25° C. at night to 8° C. to 30° C. during the day. No artificial light, photoperiodic treatments or chemical treatments were given to the plants. Plants were pinched twice. Measurements and numerical values represent averages of typical flowering types.

Botanical classification: *Clematis* hybrid 'SUZY MAC IMPROVED'.

Age of the plant described: Approximately 5 months.

Container size of the plant described: Growing in the ground.

PROPAGATION

Typical method: Vegetative cuttings.

Time to initiate rooting: Approximately 25 days at 20° C. or higher.

Time to produce a rooted plantlet: Approximately 45 to 55 days at 20° C. or higher.

Root description: Fine, fibrous.

PLANT

Growth habit: Deciduous climbing vine.

Height: Approximately 6 to 7 feet.

Plant spread: Approximately 2 to 3 feet.

Growth rate: Approximately 5 to 7 feet of growth per growing season, Spring to Fall.

Branching characteristics: One main stem.

Length of main stem: Approximately 6 to 7 feet.

Diameter of main stem: Approximately 0.2 to 0.3 cm.

Main stem color: Near RHS Greyed-Orange 165A.

Main stem texture: Glabrous at maturity. Young stems smooth with appressed hairs.

Strength: Strong, flexible, semi-woody.

FOLIAGE

Leaf:

*Arrangement.*—Opposite, mostly compound trifoliate occasionally single.

*Overall leaf length.*—Approximately 6 to 7 inches.

*Overall leaf diameter.*—Approximately 3 to 5 inches.

*Leaflets.*—Average Length: approximately 2 to 3 inches. Average Width: approximately 1 inch. Shape of blade: Lanceolate. Apex: Acute. Base: Cordate to obtuse.

*Attachment.*—Stalked, twining leaf petiole.

*Margin.*—Entire.

*Texture of upper surface.*—Smooth with distinctly hirsute veins.

*Texture of lower surface.*—Rugose, slightly pubescent toward margin.

*Durability of foliage.*—Extremely sturdy and resistant to most garden stresses.

*Color.*—Young foliage upper side: Near RHS Green 141A. Young foliage under side: Near RHS Yellow-Green 144A. Mature foliage upper side: Near RHS Green 141A. Mature foliage under side: Near RHS Green 141A.

*Venation.*—Type: Pinnate. Venation color upper side: Near RHS Green 141A. Venation color under side: Near RHS Yellow-Green 144A.

Petiole:

*Length.*—Range from 50 to 60 mm.

*Diameter.*—Approximately 0.1 to 0.3 cm.

*Texture.*—Hirsute.

*Color.*—Near RHS Greyed-Green 199A.

FLOWER

Flower buds:

*Quantity of buds per lateral stem.*—2-18.

*Shape.*—Cone shaped, with ovate base and pointed tip.

*Length.*—40-60 mm.

*Diameter.*—10-25 mm.

*Aestivation.*—Valvate.

*Color* (*at tight bud*).—Near RHS Yellow-Green 146C.

*Rate of opening.*—From bud to opening approximately 60 days.

Bloom period:

*Natural season.*—Full blooming May through June, followed by sporadic blooming until August. Another full bloom from August through September.

Quantity of flowers and buds on the plant at a given time: Each vine produces a terminal flower followed by pairs of flowers from nodes 2 to 5, 6 or 7, sometimes more, making up to 15 flowers per vine therefore several hundred flowers per plant depending on the age and size of the plant.

Inflorescence type and habit: Single occurring at terminal node, axillary nodes produce two single flowers facing outward.

Flower longevity on plant: Approximately 21 days, after fully opened. Self-cleaning.

Specific flowering:

*Inflorescence size.*—Diameter: Approximately 5 to 7 inches. Depth: Approximately 0.75 inch.

*Corolla.*—Tepal arrangement: Single whorl, moderately overlapping. Quantity: Approximately 6, occasionally 7 per flower. Shape: Broadly elliptic-ovate. Size: Length: Approximately 1.5 to 3 inches. Width: Approximately 1 to 1.5 inches. Margin: Wavy to slightly upwardly cupped. Apex: Mucronate. Base: Cuneate. Texture: Smooth. Appearance: Slight glossy sheen.

*Color.*—Tepals: When opening: Upper surface: Near RHS Violet 88A with bar near Purple-Violet N81B. Lower surface: Near RHS Violet 88A. Fully opened: Upper surface: Near RHS Violet 88A. Lower surface: Near RHS Violet 88A. Ageing: Upper Surface: Near RHS Violet 88B. Lower Surface: Near RHS Violet 88B.

*Pedicels.*—Length: Approximately 8 to 12 cm. Width: Approximately 0.3 to 0.4 cm. Angle: Nearly 90°. Strength: Strong. Color: Near RHS Green 137C.

*Fragrance.*—Faint.

REPRODUCTIVE ORGANS

Stamens:

*Number.*—70 to 90 per flower.

*Anther length.*—Approximately 5 to 9 mm.

*Anther color.*—Near RHS Violet 83B.

*Anther shape.*—Elongated, flattened, linear.

*Filament length.*—Approximately 8 to 10 mm.

*Filament color.*—Near RHS Purple-Violet N81B.

*Pollen quantity.*—Abundant.

*Pollen color.*—Near RHS White 155B.

Pistil:

*Quantity.*—35 to 45 per flower.

*Length.*—Approximately 10 to 15 mm.

*Style length.*—Approximately 10 to 15 mm.

*Stigma.*—Shape: Fine irregular hairs. Color: Near RHS White 155A.

OTHER CHARACTERISTICS

Seeds: 30 to 40, feathery seeds colored near Grey-Brown 199A.

Disease/pest resistance: Observed completely resistant to *Clematis* wilt, caused by the fungus *Ascochyta clematidina*. Neither resistance nor susceptibility to other typical diseases and pests of *Clematis* has been observed.

Temperature tolerance: Tolerates temperatures from approximately −20° C. to 27° C.

What is claimed is:

1. A new and distinct cultivar of *Clematis patens* plant named 'SUZY MAC IMPROVED' as herein illustrated and described.

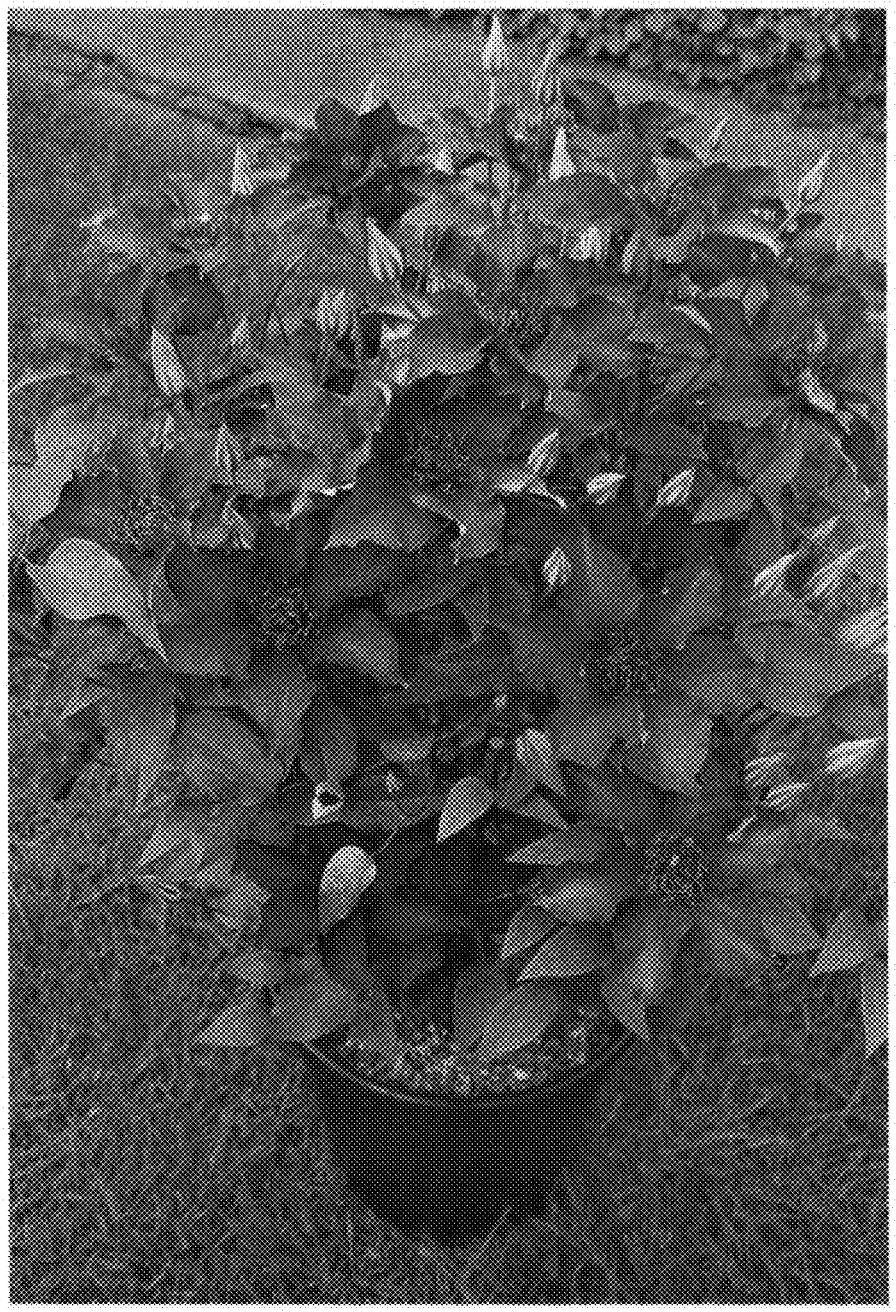

* * * * *